United States Patent [19]
Scheufler et al.

[11] Patent Number: 6,094,968
[45] Date of Patent: Aug. 1, 2000

[54] CONTINUOUS EMISSIONS MONITORING SYSTEM

[75] Inventors: Fred G. Scheufler, Schenectady; Richard D. Scheufler, East Greenbush; William H. Bayard, South Glens Falls; Nimalakirthi Rajasinghe, Mechanicville, all of N.Y.

[73] Assignee: Optimum Air Corporation, Malta, N.Y.

[21] Appl. No.: 08/899,912

[22] Filed: Jul. 24, 1997

[51] Int. Cl.[7] .............................. G01N 7/00; G01N 1/16; G06F 17/00
[52] U.S. Cl. ........................ 73/23.2; 702/77; 73/863.33
[58] Field of Search .................. 73/23.2, 31.01, 73/31.02, 863.33, 864.81; 364/496; 702/27, 30

[56] References Cited

U.S. PATENT DOCUMENTS

| | | |
|---|---|---|
| 3,043,145 | 7/1962 | Hoffman . |
| 3,860,393 | 1/1975 | Campen ................................. 73/23.2 |
| 4,090,392 | 5/1978 | Smith et al. . |
| 4,440,013 | 4/1984 | Adams . |
| 5,012,052 | 4/1991 | Hayes . |
| 5,094,099 | 3/1992 | Ross . |
| 5,270,945 | 12/1993 | Heath et al. ............................ 364/497 |
| 5,363,199 | 11/1994 | Victor et al. . |
| 5,452,234 | 9/1995 | Heath et al. ........................ 73/23.42 X |
| 5,473,162 | 12/1995 | Busch et al. . |
| 5,496,733 | 3/1996 | Spandau et al. ...................... 73/23.2 X |
| 5,521,381 | 5/1996 | Gregg et al. . |
| 5,553,496 | 9/1996 | Nishiyama et al. . |
| 5,581,017 | 12/1996 | Bejtlich, III . |
| 5,610,835 | 3/1997 | Dominguez et al. .............. 73/23.35 X |

Primary Examiner—Michael Brock
Assistant Examiner—Jay L. Politzer
Attorney, Agent, or Firm—Schmeiser, Olsen & Watts

[57] ABSTRACT

A continuous emissions monitoring system for continuously monitoring and evaluating air flow samples from a plurality of emission sites. The monitoring system includes a microprocessor controlled Fourier transform infrared scanning laser system for identifying and quantifying compounds in the air flow samples based on known spectral absorption bands. The monitoring system also includes an auxiliary gas chromatograph for separating and analyzing compounds belonging to a common family which exhibit interference patterns or overlapping spectral bands. The auxiliary gas chromatograph is employed in cases where the infrared scanning laser system detects high levels of compounds, above a predetermined threshold level, exhibiting such interference patterns, or when an unknown compound is detected by the infrared scanning laser system. A sampling station continuously and simultaneously draws air flow samples from the plurality of emission sites, such that an air flow sample from any of the plurality of emission sites is immediately available for analysis.

5 Claims, 2 Drawing Sheets

CONTINUOUS EMISSIONS MONITORING SYSTEM

FIELD OF THE INVENTION

The present invention is in the field of emissions monitoring. More particularly, the present invention provides a system for rapidly and accurately monitoring and evaluating compounds in the air flow from a plurality of emission sites.

BACKGROUND OF THE INVENTION

A wide variety of emissions monitoring systems are available in the prior art. Unfortunately, these systems are typically designed to be compound specific, where only a relatively small number of compounds are detected and/or monitored in an air flow sample from an emission site. Further, these systems are commonly designed to draw and monitor air flow samples from a plurality of emission sites in a sequential manner, potentially introducing large cycle time delays in the monitoring process. This can be especially problematic if many of the emission sites are located a large distance away from the emission monitoring system.

SUMMARY OF THE INVENTION

The continuous emissions monitoring system of the present invention is designed to continuously monitor and evaluate air flow samples from a plurality of emission sites. The monitoring system uses a primary analysis unit, preferably comprising a microprocessor controlled Fourier transform infrared scanning laser system, to identify, analyze and quantify compounds in the air flow samples based on their known spectral absorption bands. The monitoring system also employs an auxiliary analysis unit, such as a gas chromatograph, to separate and analyze compounds belonging to a common family which exhibit interference patterns or overlapping spectral bands, and to analyze and identify unknown compounds. The gas chromatograph is typically employed in cases where the infrared scanning laser system detects high levels of compounds exhibiting such interference patterns, or in cases where the infrared scanning laser system is unable to identify a compound.

The continuous emissions monitoring system also includes a detection system for immediately detecting the gross level of compounds present within each emission site. The detection system preferably comprises a photo ionization detector (PID) which provides a count (e.g., in parts per million) of the compounds present in a testing location.

The photo ionization detector used in the detection system of the present invention does not identify the specific compounds present at an emission site. Rather, the photo ionization detector provides an indication of the total level of all compounds at an emission site. The output level of each photo ionization detector is monitored to determine if the level of compounds within a corresponding emission site falls within an expected range or exceeds one or more predetermined levels. If the output level of a specific photo ionization detector exceeds a predetermined threshold level, possibly indicating a system malfunction or the presence of an unknown or unexpected compound at an emission site, an air flow sample from that emission site is immediately provided to the primary and/or auxiliary analysis unit for identification, analysis, and quantification.

Unlike prior art emission testing systems, the continuous emissions monitoring system of the present invention is designed to continuously and simultaneously draw air flow samples from a plurality of emission sites. Thus, an air flow sample from each emission site is immediately available for analysis by the primary and/or auxiliary analysis units. Advantageously, this reduces the sample draw times and sample cycle times required to sequentially test an air flow sample from each of a plurality of emission sites, thereby drastically reducing the time required for evaluation.

BRIEF DESCRIPTION OF THE DRAWINGS

The features of the present invention will best be understood from a detailed description of the invention and preferred embodiments thereof selected for the purposes of illustration and shown in the accompanying drawings in which.

DETAILED DESCRIPTION OF THE INVENTION

Figure 1:
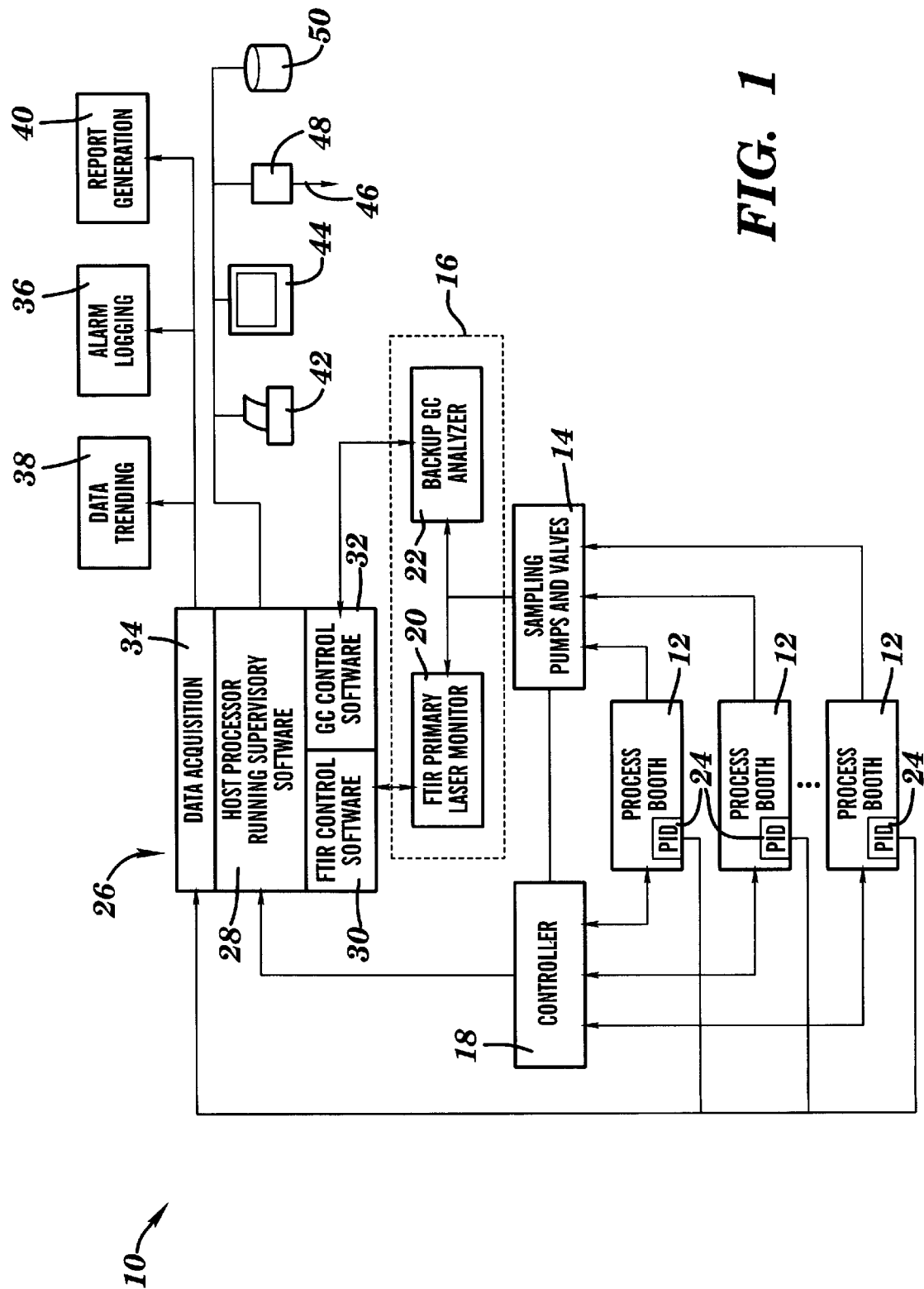
FIG. 1 is a block diagram of a continuous emissions monitoring system in accordance with a preferred embodiment of the present invention.

The features and advantages of the present invention are illustrated in detail in the accompanying drawings, wherein like reference numerals refer to like elements throughout the drawings.

A continuous emissions monitoring system, generally designated as 10, is illustrated in block form in FIG. 1. The monitoring system 10 is designed to monitor and evaluate compounds in the air flow samples from at least one emission site 12. The air flow from any type of emission site, such a paint spray booth, a paint drying booth, or the like, can be evaluated using the continuous emissions monitoring system 10 of the present invention.

A sampling station 14 directs air flow samples from each emission site 12 to a monitoring station 16 for analysis. An air sample controller 18, coupled to each emission site 12 and the sampling station 14, selectively controls the passage of air flow samples from each emission site 12 to the monitoring station 16. Preferably, the sampling station 14 employs a sample draw technique whereby air flow samples from all of the emission sites 12 are continuously and simultaneously available at the monitoring station 16 for analysis. Advantageously, this eliminates cycle time delays caused by drawing air flow samples from each emission site 12 in a sequential manner over long distances.

The monitoring station 16 includes a primary analysis unit 20, preferably comprising a microprocessor controlled Fourier transform infrared scanning laser system (FTIR) of a type known in the art, to identify, analyze, and quantify compounds in the air flow samples based on their known spectral absorption bands. This technique provides for precise analysis of compounds having a wide range of molecular weights, including light alcohols, glycols, amines, and heavy aromatics.

In some cases, interference patterns or overlapping spectral bands corresponding to a common family of compounds are observed by the primary analysis unit 20. When the primary analysis unit 20 detects high levels of compounds displaying such interference patterns, above a predetermined threshold level, an auxiliary analysis unit 22 is employed to separate and analyze the members of each common family of compounds. Preferably, a gas chromatograph (GC) of a type known in the art is used as the auxiliary analysis unit 22. The gas chromatograph may contain a plurality of separate analytical columns to allow accurate separation and analysis of each family of compounds detected by the primary analysis unit 20. The auxiliary analysis unit 22 may also be used to identify and analyze unknown compounds in the air flow samples.

The continuous emissions monitoring system 10 also includes a detection system for continuously monitoring the compounds present at each emission site 12. The detection system preferably comprises a plurality of photo ionization detectors (PID) 24 which provide a measure of the gross level of compounds present at each emission site. The output of each photo ionization detector 24 is continuously acquired and monitored by a host processor 26. The host processor 26 continually analyzes the output level of each photo ionization detector 24 to determine if the level of compounds within each emission site 12 falls within an expected operating range or exceeds one or more predetermined levels. If the output level of a photo ionization detector 24 exceeds a predetermined level, possibly indicating, for example, a system malfunction or the presence of an unknown or unexpected compound at a corresponding emission site 12, an air flow sample from that emission site 12 is immediately provided to the primary analysis unit 20 and/or the auxiliary analysis unit 22 by the sampling station 14 for further analysis.

The host processor 26 supervises the overall operation of the continuous emissions monitoring system 10. The host processor 26 runs the supervisory software 28 necessary for the integration and automation of the functions of the primary analysis unit 20, the auxiliary analysis unit 22, the photo ionization detectors 24, and the air sample controller 18. The FTIR software 30 and GC software 32 required for the operation of the primary analysis unit 20 and auxiliary analysis unit 22, respectively, as well as the data acquisition software 34 required for the acquisition of the data produced by the photo ionization detectors 24, also run on the host processor 26.

The host processor 26 provides a user with a wide variety of system information through the use of an alarm logging system 36, a data trend analysis system 38, and a report generation system 40. The output of the alarm logging system 36, the data trend analysis system 38, and the report generation system 40 may be provided in hardcopy form on a printer 42, visually on a display 44, or transmitted to a remote location 46 via a modem 48 Preferably, at least some of the data produced by the continuous emissions monitoring system 10 is archived on a memory unit 50.

The alarm logging system 36 records, and maintains a chronological history of, alarm conditions sensed by the host processor 26. An alarm condition may be generated, for example, by a malfunction in a portion of the continuous emissions monitoring system 10, or may be due to a problem at an emission site 12. In the latter case, the alarm condition may indicate the presence of an unacceptable level of a compound in the air flow from an emission site 12, indicating a potential problem in the operation and/or performance of that emission site 12.

The data trend analysis system 38 detects trends in the operational performance of the continuous emissions monitoring system 10 for maintenance purposes. The data trend analysis system 38 may also be used to detect trends in the levels of compounds detected in the air flow from the emission sites 12 by the monitoring station 16. For instance, a gradual increase in the detected levels of one or more compounds in the air flow from an emission site 12 may indicate that the performance of that emission site has degraded below an acceptable level.

Figure 2:
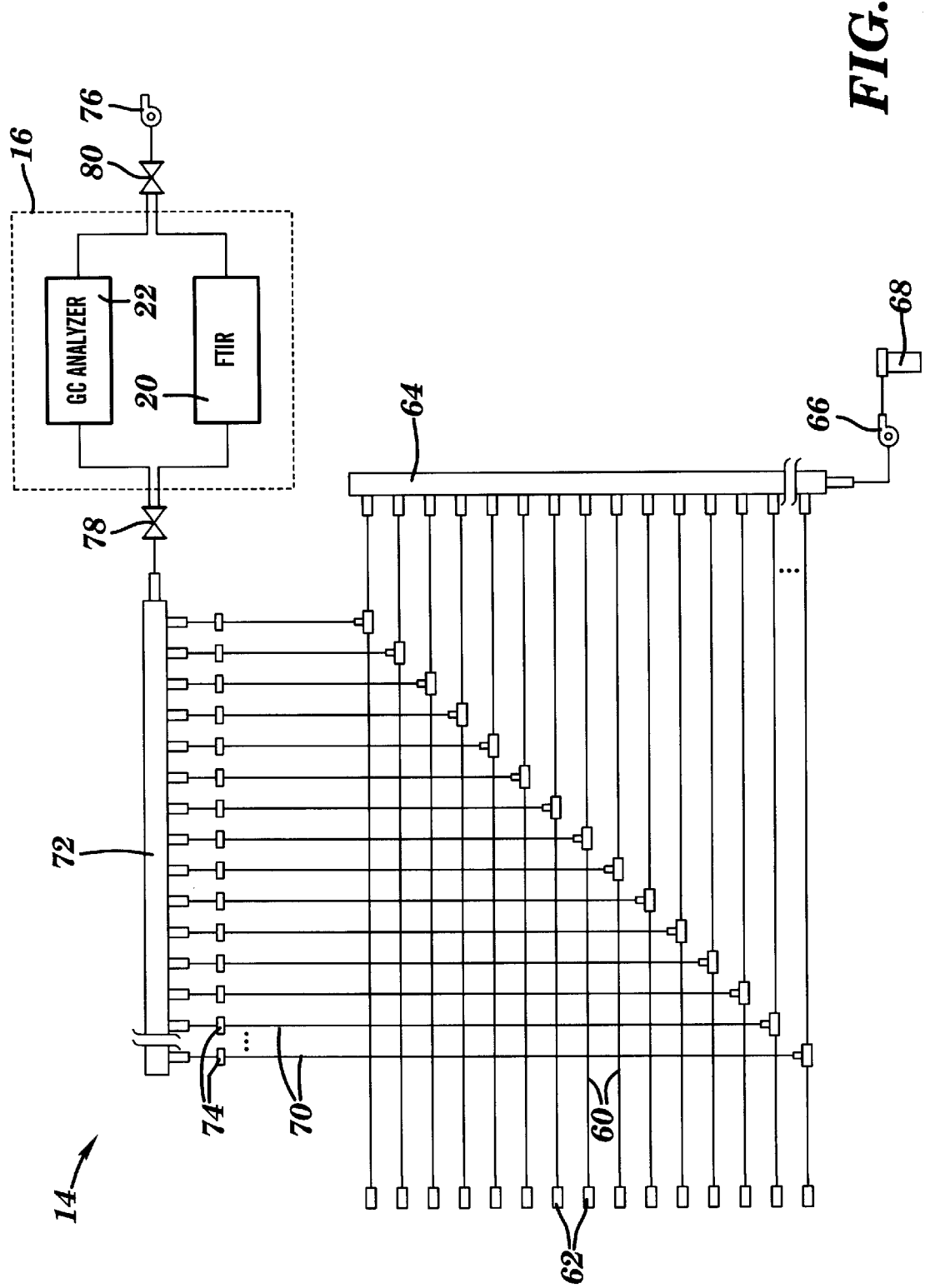
FIG. 2 illustrates a sampling system for sampling the emissions from a plurality of emission sites

The sampling station 14 is illustrated in greater detail in FIG. 2. A plurality of individual source lines 60 extend from a sample port 62 at each emission site 12 to a source draw manifold header 64. Air flow samples from each emission site 12 are continuously and simultaneously drawn through the source lines 60 into the source draw manifold header 64 by a source draw pump 66. In this manner, air flow samples from all of the emission sites 12 are immediately available for analysis by the monitoring station 16. The individual air flow samples in the source lines 60 are combined in the source draw manifold header 64 and passed out of the sampling station 14 through a carbon canister 68.

A sample line 70 extends from each source line 60 to a sample draw manifold header 72. A plurality of sampling valves 74, each located on a sample line 70, are used to selectively isolate an direct an air flow sample from a specific one of the sample lines 70 to the monitoring station 16 for analysis. The sampling valves 74 are individually actuated in response to commands provided by the air sample controller 18 (FIG. 1).

During normal operation of the continuous emissions monitoring system 10, the sampling valves 74 are preferably repeatedly actuated in a sequential manner to direct air flow samples from each of the emission sites 12 into the monitoring station 16 for analysis. In cases where a photo ionization detector 24 detects an abnormal condition in a specific emission site 12, the sampling valve 74 connected to the source line 60 from that emission site may be selectively activated by the air sample controller 18 (under control of the host processor 26) to immediately provide an air flow sample from that emission site 12 to the monitoring station 16.

An air flow sample from an emission site 12 is drawn into the monitoring station 16 by a sample draw pump 76. A first diverter valve 78 selectively diverts the air flow sample into either the primary analysis unit 20 or the auxiliary analysis unit 22, depending on which type of analysis is required. Preferably, an air flow sample is initially passed into the primary analysis unit 20 for analysis. If certain conditions exist, such as the presence of a family of compounds or an unidentifiable compound in the air flow sample, the sample is diverted by the first diverter valve 78 into the auxiliary analysis unit 22 for further examination. After analysis, the air flow sample is drawn out of the selected analysis unit 20 or 22 through a second diverter valve 80 by the sample draw pump 76.

The foregoing description of the present invention has been presented for purposes of illustration and description. It is not intended to be exhaustive or to limit the invention to the precise form disclosed, and many modifications and variations are possible in light of the above teaching. Such modifications and variations that may be apparent to a person skilled in the art are intended to be included within the scope of this invention as defined by the accompanying claims.

We claim:

1. A method for continuously monitoring emissions from a plurality of emission sites, comprising the steps of:

providing a plurality of source lines, each source line extending from a respective one of said plurality of emission sites;

continuously and simultaneously drawing air flow samples from the plurality of emission sites through said plurality of source lines;

providing a plurality of sample lines, each sample line extending from a respective one of said plurality of source lines;

providing a detection system for detecting a gross level of compounds within each of the plurality of emission sites; and selectively providing an air flow sample from an emission site to said monitoring station through one of said plurality of sample lines if the gross level of compounds in that emission site exceeds a predetermined threshold.

2. The method according to claim 1, wherein said monitoring station includes a primary analysis unit and an auxiliary analysis unit, further including the steps of:

identifying and quantifying a first set of compounds in each of said air flow samples using the primary analysis unit;

detecting a presence of a second set of compounds in each of said air flow samples using the primary analysis unit, and providing the air flow samples containing said second set of compounds to the auxiliary analysis unit for identification and quantification of said second set of compounds.

3. The method according to claim 2, wherein said providing step further includes the step of:

selectively providing an air flow sample containing said second set of compounds to the auxiliary analysis unit when the primary analysis unit detects predetermined levels of the second set of compounds in that air flow sample.

4. The method according to claim 2, wherein said second set of compounds includes compounds belonging to a common family of compounds.

5. The method according to claim 2, wherein an air flow sample is selectively provided to the auxiliary analysis unit when the primary analysis unit detects an unknown compound in that air flow sample.

* * * * *